(12) United States Patent
Kuramochi

(10) Patent No.: US 11,819,342 B2
(45) Date of Patent: Nov. 21, 2023

(54) ORAL MEASUREMENT APPARATUS AND SYSTEM

(71) Applicant: Murata Manufacturing Co., Ltd., Nagaokakyo (JP)

(72) Inventor: Yoshie Kuramochi, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 449 days.

(21) Appl. No.: 17/093,973

(22) Filed: Nov. 10, 2020

(65) Prior Publication Data
US 2021/0153812 A1 May 27, 2021

(30) Foreign Application Priority Data

Nov. 25, 2019 (JP) .................................. 2019-212477

(51) Int. Cl.
*A61B 5/00* (2006.01)
*G01N 27/60* (2006.01)
(Continued)

(52) U.S. Cl.
CPC .............. *A61B 5/6847* (2013.01); *A61B 5/01* (2013.01); *A61B 5/4875* (2013.01); *G01K 7/16* (2013.01);
(Continued)

(58) Field of Classification Search
CPC .......... A61B 2562/0271; A61B 5/6846; A61B 5/6847; A61B 5/01; A61B 5/4875;
(Continued)

(56) References Cited

U.S. PATENT DOCUMENTS 8,911,380 B1 * 12/2014 Feldman .............. A61B 5/0878 600/536
9,366,580 B2 * 6/2016 Hocker .................. G01N 33/12
(Continued)

FOREIGN PATENT DOCUMENTS

JP       H0856907 A     3/1996
JP     2003334173 A    11/2003
(Continued)

OTHER PUBLICATIONS

Japanese Office Action issued for JP Patent Application No. 2019-212477, dated Feb. 1, 2022.

*Primary Examiner* — May A Abouelela
(74) *Attorney, Agent, or Firm* — ArentFox Schiff LLP

(57) ABSTRACT

An oral measurement apparatus that extends in a longitudinal direction and includes a sensor, a processor, and a temperature information obtaining section. The sensor is disposed at a first end of the oral measurement apparatus in the longitudinal direction and obtains analog information inside a mouth. The processor is disposed closer to the sensor with respect to a central portion of the oral measurement apparatus in the longitudinal direction. The processor converts the analog information obtained by the sensor into digital information and outputs the digital information as a processing result. The temperature information obtaining section obtains temperature information indicating a temperature of the processor and outputs the temperature information.

20 Claims, 12 Drawing Sheets

1A

(51) Int. Cl.
  *A61B 5/01* (2006.01)
  *G01K 7/16* (2006.01)
(52) U.S. Cl.
  CPC .... *G01N 27/605* (2013.01); *A61B 2562/0271* (2013.01)
(58) Field of Classification Search
  CPC .......... A61B 5/48; A61B 5/4277; G01K 7/16; G01K 1/16; G01K 13/20; G01K 13/00; G01N 27/605
  See application file for complete search history.

(56) References Cited

U.S. PATENT DOCUMENTS

| | | | | |
|---|---|---|---|---|
| 2001/0005791 | A1* | 6/2001 | Ginsburg | A61M 25/00 607/113 |
| 2004/0015094 | A1 | 1/2004 | Manabe et al. | |
| 2005/0234365 | A1* | 10/2005 | Sonis | A61B 5/682 600/547 |
| 2009/0272201 | A1* | 11/2009 | Loeb | G01L 5/228 73/862.041 |
| 2010/0103624 | A1* | 4/2010 | Chen | H01L 23/34 361/710 |
| 2011/0222579 | A1* | 9/2011 | Yu | A61B 5/01 374/E1.001 |
| 2013/0120630 | A1* | 5/2013 | Kim | H04N 23/63 348/E5.022 |
| 2013/0121375 | A1* | 5/2013 | Yu | G01K 7/02 374/170 |
| 2014/0018641 | A1 | 1/2014 | Yoshino et al. | |
| 2014/0278202 | A1* | 9/2014 | Anderson | F24C 7/087 702/136 |
| 2016/0048180 | A1* | 2/2016 | Woo | G06F 1/206 361/679.48 |
| 2016/0293513 | A1* | 10/2016 | Hiruta | H01L 23/3128 |
| 2017/0035316 | A1* | 2/2017 | Kuzniecky | A61B 5/0002 |
| 2017/0074729 | A1* | 3/2017 | Coutts | G06F 1/3206 |
| 2017/0143419 | A1* | 5/2017 | Ingle | A61B 18/1492 |
| 2017/0199084 | A1* | 7/2017 | Kimura | G01K 1/14 |
| 2017/0205365 | A1* | 7/2017 | Cavallaro | G01K 7/425 |
| 2017/0281010 | A1* | 10/2017 | Saeidi | G06F 1/206 |
| 2017/0294784 | A1* | 10/2017 | King | H02J 7/00 |
| 2018/0143080 | A1* | 5/2018 | Yu | G05D 23/1919 |
| 2018/0220898 | A1* | 8/2018 | Muehlbauer | A61B 5/02055 |
| 2018/0288547 | A1* | 10/2018 | Lasseuguette | B81B 7/008 |
| 2018/0321999 | A1* | 11/2018 | Kubota | G06F 11/0751 |
| 2019/0025134 | A1* | 1/2019 | Ju | G01K 1/14 |
| 2019/0038174 | A1 | 2/2019 | Shenhav et al. | |
| 2019/0142332 | A1* | 5/2019 | Bonifas | A61B 5/4875 600/549 |
| 2019/0157904 | A1* | 5/2019 | Qian | H02J 3/02 |
| 2019/0261889 | A1* | 8/2019 | White | A61B 5/682 |
| 2019/0310694 | A1* | 10/2019 | Davis | G01K 13/00 |
| 2019/0313907 | A1* | 10/2019 | Khachaturian | G16H 40/67 |
| 2019/0321613 | A1* | 10/2019 | Jones | A61M 31/002 |
| 2019/0350469 | A1* | 11/2019 | Khachaturian | A61B 5/0008 |
| 2020/0014326 | A1* | 1/2020 | Miller | G01K 7/18 |
| 2020/0094689 | A1* | 3/2020 | Myer | H01R 13/639 |
| 2020/0113729 | A1* | 4/2020 | Doran | G16H 40/60 |
| 2021/0399682 | A1* | 12/2021 | Kubo | H02S 50/00 |
| 2022/0253160 | A1* | 8/2022 | Williams | G06F 3/03543 |

FOREIGN PATENT DOCUMENTS

| | | |
|---|---|---|
| JP | 2017028803 A | 2/2017 |
| JP | 2018191717 A | 12/2018 |
| JP | 2019025133 A | 2/2019 |
| JP | 2019511932 A | 5/2019 |
| WO | 2004028359 A1 | 4/2004 |
| WO | 2012124330 A1 | 9/2012 |
| WO | 2014041585 A1 | 3/2014 |

\* cited by examiner

ORAL MEASUREMENT APPARATUS AND SYSTEM

CROSS REFERENCE TO RELATED APPLICATIONS

The present application claims priority to Japanese Patent Application No. 2019-212477, filed Nov. 25, 2019, the entire contents of each of which are incorporated herein by reference.

TECHNICAL FIELD

The present invention relates to an oral measurement apparatus and system.

BACKGROUND

International Publication No. 2004/028359 discloses an instrument for measuring the amount of moisture in a person's (or animal's) mouth. This instrument includes a sensor unit and a measuring unit. The sensor unit is brought into contact with a part to be measured directly or via a plastic film and determines the amount of moisture in this part. The measuring unit includes this sensor unit.

Currently, there is an increasing demand for an oral measurement apparatus and system that can obtain temperature information.

SUMMARY OF THE INVENTION

According to an exemplary aspect of the present invention, an oral measurement apparatus is provided that extend in a longitudinal direction. The oral measurement apparatus includes a sensor, a processor, and a temperature information obtaining section. The sensor is disposed at a first end of the oral measurement apparatus in the longitudinal direction and obtains analog information inside a mouth. The processor is disposed close to the sensor with respect to a central portion of the oral measurement apparatus in the longitudinal direction. Moreover, the processor is configured to convert the analog information obtained by the sensor into digital information and output the digital information as a processing result. The temperature information obtaining section obtains temperature information indicating a temperature of the processor and outputs the temperature information.

According to an exemplary aspect of the present invention, an oral measurement system is also provided. In this aspect, the oral measurement system includes an oral measurement apparatus extending in a longitudinal direction and a processing device that communicates with the oral measurement apparatus. The oral measurement apparatus includes a sensor, a processor, a temperature information obtaining section, and a first communication unit. The sensor is disposed at a first end of the oral measurement apparatus in the longitudinal direction and obtains analog information inside a mouth. The processor is disposed close to the sensor with respect to a central portion of the oral measurement apparatus in the longitudinal direction. The processor is configured to convert the analog information obtained by the sensor into digital information and output the digital information as a processing result. The temperature information obtaining section obtains temperature information indicating a temperature of the processor and outputs the temperature information. The first communication unit sends the processing result and the temperature information to the processing device. The processing device includes a second communication unit, a calculator, and a correction processor. The second communication unit receives the processing result and the temperature information from the first communication unit of the oral measurement apparatus. The calculator is further configured to calculate a level of a subject in the mouth based on the processing result. The correction processor corrects the calculated level of the subject, based on information indicating the calculated level of the subject and the temperature information.

According to an exemplary aspect of the present invention, an oral measurement apparatus and system is provided that obtains temperature information.

Other features, elements, characteristics and advantages of the exemplary embodiments will become more apparent from the following detailed description of the present invention with reference to the attached drawings.

DETAILED DESCRIPTION OF THE EMBODIMENTS

Figure 1:
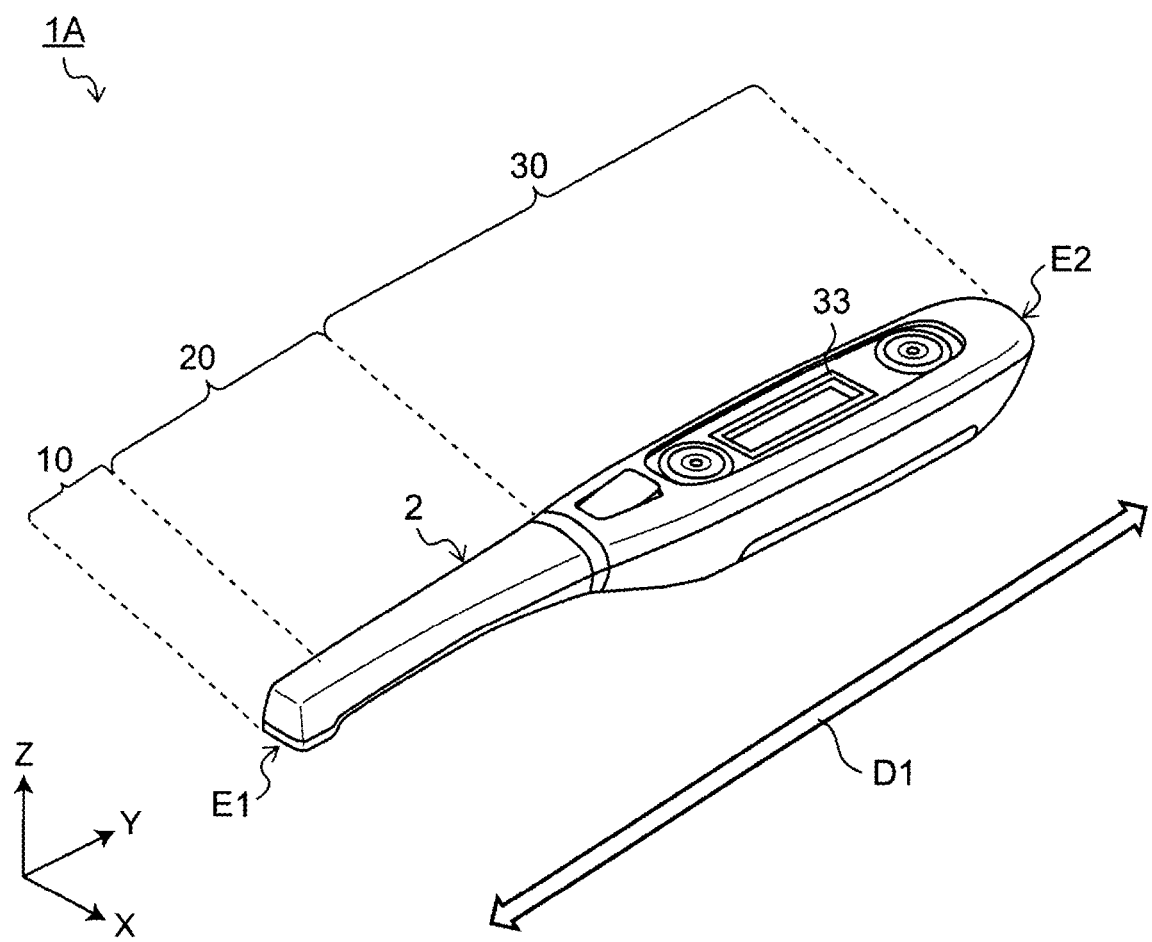
FIG. 1 is a schematic perspective view illustrating an example of an oral measurement apparatus according to a first exemplary embodiment.

A sensor measuring the level of a subject in a mouth, such as the moisture-amount measuring instrument disclosed in International Publication No. 2004/028359, is known. This instrument measures the amount of moisture in the mouth by bringing the sensor unit into contact with a part to be measured in the mouth directly or via a plastic film.

An oral measurement apparatus, such as the above-described instrument, contacts the mouth of a user, which may increase the temperature of the apparatus. This may also change the temperature of a processor that processes information inside the mouth obtained by the sensor, thereby causing variations in the measurement values of the amount of moisture.

To address this issue, a temperature information obtaining section that obtains temperature information is disclosed herein.

More particularly, according to an exemplary aspect, an oral measurement apparatus is provided that is extending in a longitudinal direction. The oral measurement apparatus includes a sensor, a processor, and a temperature information obtaining section. The sensor is disposed at a first end of the oral measurement apparatus in the longitudinal direction and obtains analog information inside a mouth. The processor is disposed close to the sensor with respect to a central portion of the oral measurement apparatus in the longitudinal direction. The processor converts the analog information obtained by the sensor into digital information and outputs the digital information as a processing result. The temperature information obtaining section obtains temperature information indicating a temperature of the processor and outputs the temperature information.

This configuration enables temperature information to be obtained that indicates the temperature of the processor.

The oral measurement apparatus can further include a casing that stores the sensor, the processor, and the temperature information obtaining section therein. The casing can also include a sensor unit, a holding portion, and a probe unit. The sensor unit is disposed close to the first end of the oral measurement apparatus in the longitudinal direction. The holding portion is disposed close to a second end of the oral measurement apparatus in the longitudinal direction. The probe unit is formed in a bar-like shape and connects the sensor unit and the holding portion with each other with the probe unit interposed therebetween. The sensor can be disposed in or on the sensor unit. The processor and the temperature information obtaining section may be disposed within the probe unit.

This configuration makes it easier to bring the sensor into contact with the inside of the mouth and also to obtain temperature information concerning the processor with high accuracy.

The temperature information obtaining section may be disposed closer to the second end of the oral measurement apparatus in the longitudinal direction than the processor is.

This configuration can reduce the occurrence of noise.

The processor and the temperature information obtaining section may contact each other via a heat transfer member.

This configuration makes it possible to enhance thermal coupling between the processor and the temperature information obtaining section. The temperature information obtaining section is thus able to obtain the temperature information concerning the processor with high accuracy.

The heat transfer member may be one of a substrate, a metal member, silicone, and carbon.

This makes it possible to obtain the temperature information concerning the processor with even higher accuracy.

The heat transfer member may be a ground pattern of the substrate.

This configuration can reduce the number of components of the oral measurement apparatus while enhancing thermal coupling between the processor and the temperature information obtaining section.

The processor and the temperature information obtaining section may be sealed with a heat transfer resin member.

This configuration makes it possible to protect the processor and the temperature information obtaining section from damage caused by an external load while enhancing thermal coupling between the processor and the temperature information obtaining section.

The oral measurement apparatus may further include a calculator that is configured to calculate a level of a subject in the mouth, based on the processing result output from the processor.

With this configuration, the level of the subject in the mouth can be measured.

The oral measurement apparatus may further include a correction processor that is configured to correct the calculated level of the subject, based on information indicating the calculated level of the subject and the temperature information.

With this configuration, the calculated level of the subject can be corrected based on the temperature information concerning the processor.

The level of the subject may be an amount of moisture.

With this configuration, the amount of moisture in the mouth can be measured.

According to another exemplary aspect, an oral measurement system is provided that includes an oral measurement apparatus extending in a longitudinal direction and a processing device that communicates with the oral measurement apparatus. The oral measurement apparatus includes a sensor, a processor, a temperature information obtaining section, and a first communication unit. The sensor is disposed at a first end of the oral measurement apparatus in the longitudinal direction and obtains analog information inside a mouth. The processor is disposed close to the sensor with respect to a central portion of the oral measurement apparatus in the longitudinal direction. The processor is configured to convert the analog information obtained by the sensor into digital information and outputs the digital information as a processing result. The temperature information obtaining section obtains temperature information indicating a temperature of the processor and outputs the temperature information. The first communication unit sends the processing result and the temperature information to the processing device. The processing device includes a second communication unit, a calculator, and a correction processor. The second communication unit receives the processing result and the temperature information from the first communication unit of the oral measurement apparatus. The calculator is configured to calculate a level of a subject in the mouth based on the processing result. The correction processor is configured to correct the calculated level of the subject, based on information indicating the calculated level of the subject and the temperature information.

This configuration makes it possible to obtain temperature information indicating the temperature of the processor and also to correct the calculated level of the subject based on the temperature information.

Exemplary embodiments will be described below with reference to the accompanying drawings. The embodiments described below are merely examples of the invention and are not intended to limit the disclosure, applications, and purposes of the invention. It is also noted that the drawings are only schematically shown, and the dimensional ratio of each component and the dimensional ratio of one component to that of another component shown in the drawings do not necessarily match the actual ratios.

First Exemplary Embodiment

[Overall Configuration]

Figure 2:
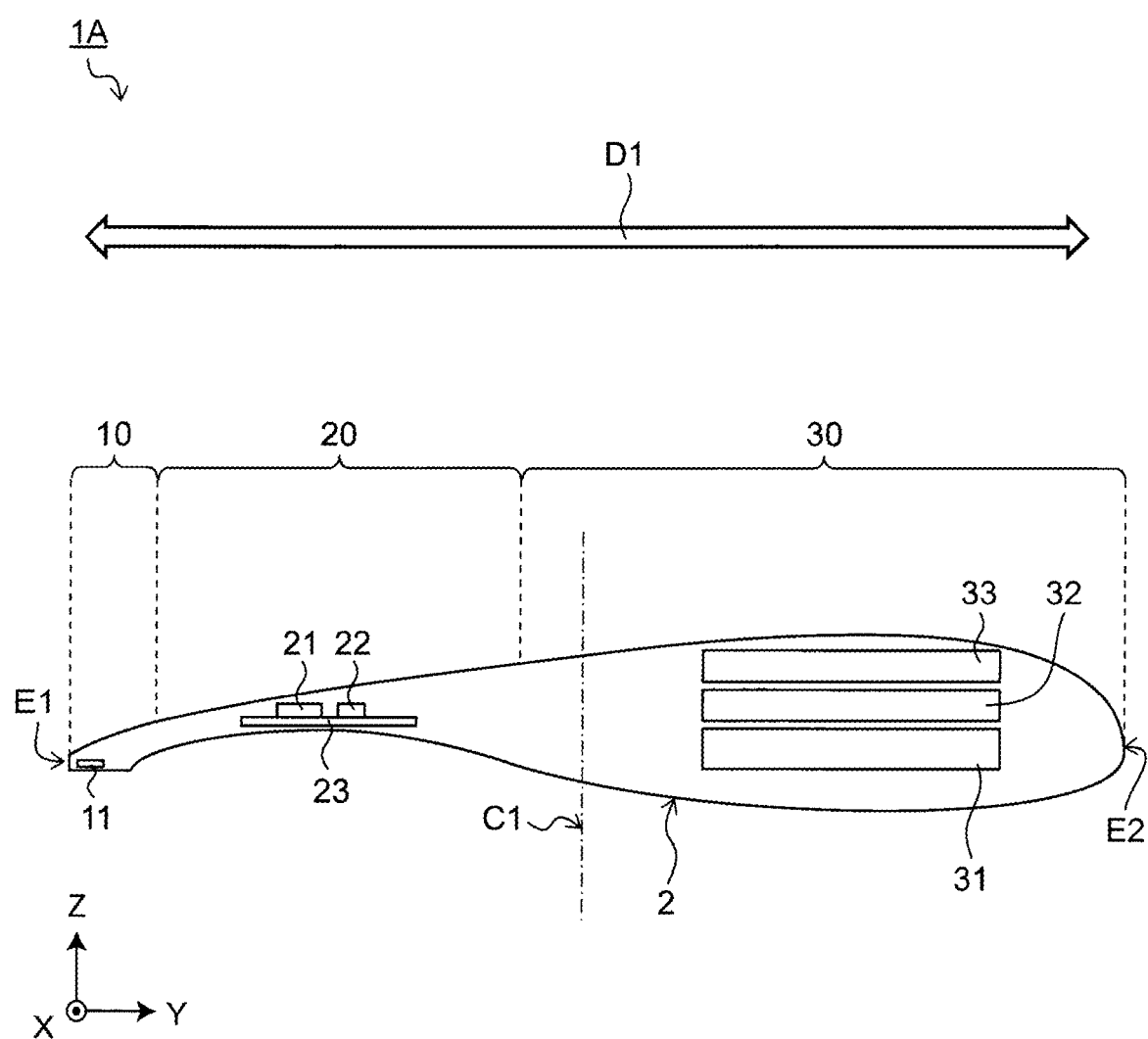
FIG. 2 is a schematic view illustrating an example of the internal configuration of the oral measurement apparatus according to the first exemplary embodiment.
Figure 3:
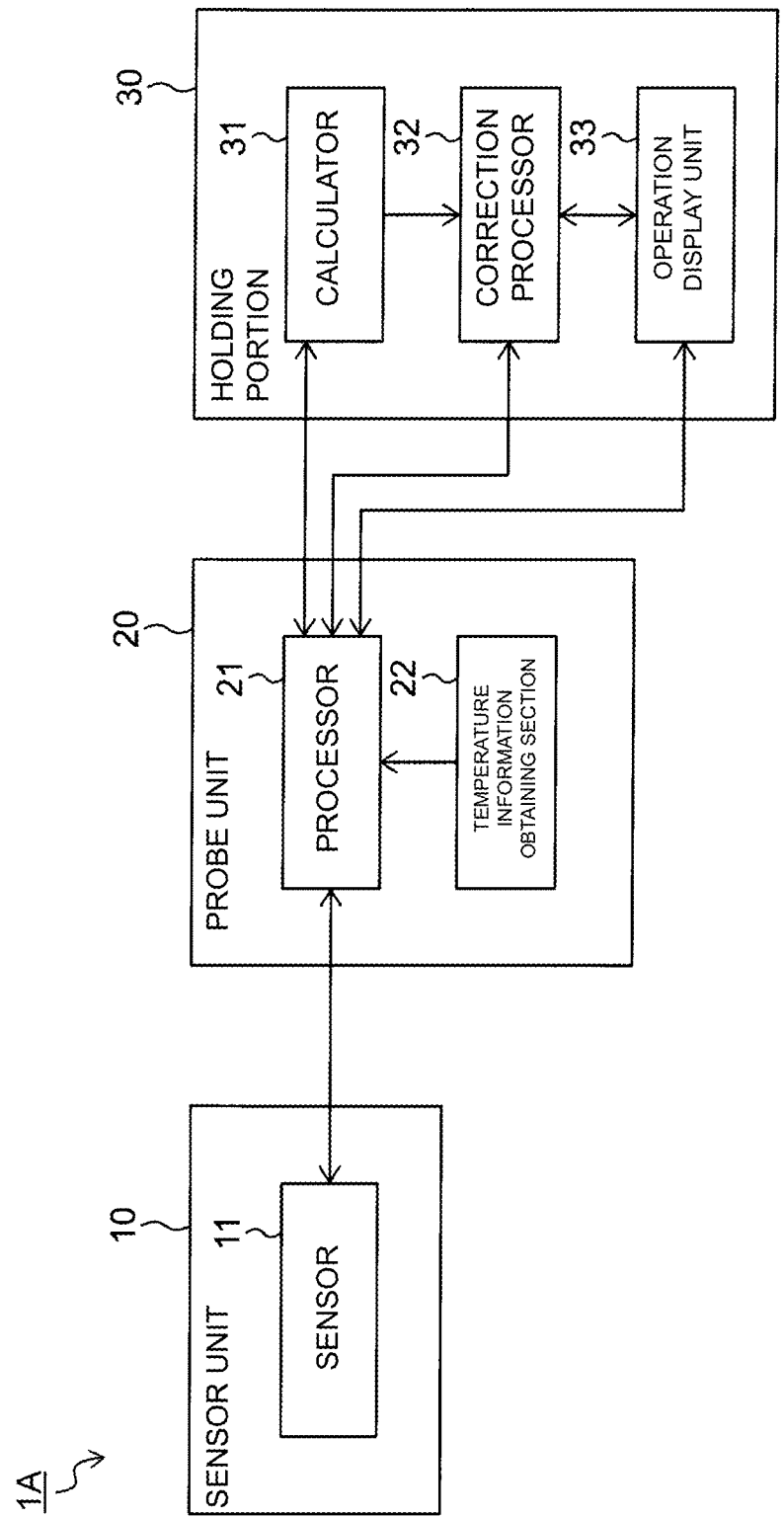
FIG. 3 is a block diagram illustrating an example of the schematic configuration of the oral measurement apparatus according to the first exemplary embodiment.

FIG. 1 is a schematic perspective view illustrating an example of the configuration of an oral measurement apparatus 1A according to a first exemplary embodiment. FIG. 2 is a schematic view illustrating an example of the internal configuration of the oral measurement apparatus 1A. FIG. 3 is a block diagram illustrating an example of the schematic configuration of the oral measurement apparatus 1A. The directions indicated by X, Y, and Z in the drawings represent the width, the length, and the height of the oral measurement apparatus 1A.

{External Appearance}

The external appearance of the oral measurement apparatus 1A will be explained below. As shown in FIGS. 1 and 2, the oral measurement apparatus 1A includes a casing 2. The casing 2 is formed in a bar-like shape extending in the longitudinal direction D1. The casing 2 includes a sensor unit 10, a probe unit 20, and a holding portion 30.

The sensor unit 10 is a portion that is constructed to contact the inside of the mouth of a user when the measurement is conducted with the oral measurement apparatus 1A. The sensor unit 10 is disposed close to a first end E1 (e.g., one end) of the oral measurement apparatus 1A in the longitudinal direction D1. The external dimensions of the sensor unit 10 are designed to be smaller than those of the probe unit 20 and the holding portion 30. For example, the dimensions of the sensor unit 10 in the X and Y directions are smaller than those of the probe unit 20 and the holding portion 30.

The probe unit 20 connects the sensor unit 10 and the holding portion 30 with each other with the probe unit 20 interposed therebetween. The probe unit 20 is formed in a bar-like shape. The dimensions of the probe unit 20 in the X and Z directions become smaller in the direction from the holding portion 30 toward the sensor unit 10. That is, the probe unit 20 is formed in a shape which tapers down from the holding portion 30 toward the sensor unit 10.

The holding portion 30 is configured to be held by a user and is positioned outside the mouth of a user when the measurement is conducted with the oral measurement apparatus 1A. The holding portion 30 is disposed close to a second end E2 (e.g. a second or the other end) of the oral measurement apparatus 1A in the longitudinal direction D1. The holding portion 30 is formed in a bar-like shape. The external dimensions of the holding portion 30 are designed to be larger than those of the sensor unit 10 and the probe unit 20. For example, the dimensions of the holding portion 30 in the X, Y, and Z directions are larger than those of the sensor unit 10 and the probe unit 20.

The casing 2 is made of a resin in an exemplary aspect. Moreover, the entirety or part of the casing 2 may be made of a metal, for example.

The elements forming the oral measurement apparatus 1A will be discussed below. As shown in FIGS. 1 through 3, the oral measurement apparatus 1A includes a sensor 11, a processor 21, a temperature information obtaining section 22, a substrate 23, a calculator 31, a correction processor 32, and an operation display unit 33.

In the first embodiment, the substrate 23, the calculator 31, the correction processor 32, and the operation display unit 33 are provided in the oral measurement apparatus 1A. However, this configuration is only an example, and these elements may be provided in a device different from the oral measurement apparatus 1A.

In the first embodiment, the subject to be measured by the oral measurement apparatus 1A is moisture, and the measurement of moisture using the oral measurement apparatus 1A will be discussed below through illustration of an example.

{Sensor}

The sensor 11 is constructed to obtain analog information inside a mouth. In the first embodiment, the sensor 11 is a capacitive sensor, for example. The sensor 11 is brought into contact with the inside of the mouth so as to obtain information indicating the electrostatic capacity as analog information inside the mouth.

Figure 4:
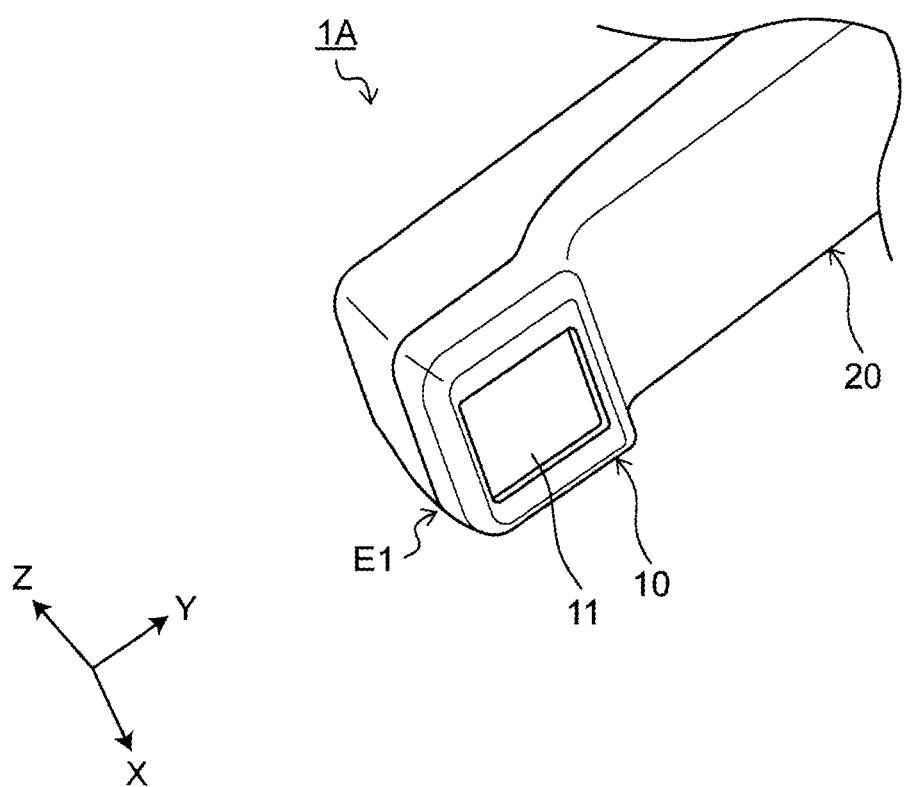
FIG. 4 is a schematic perspective view illustrating an example of a sensor of the oral measurement apparatus according to the first exemplary embodiment.

The sensor 11 is disposed at the first end E1 of the oral measurement apparatus 1A in the longitudinal direction D1. FIG. 4 is a schematic perspective view illustrating an example of the sensor 11 of the oral measurement apparatus 1A. As shown in FIG. 4, the sensor 11 is disposed on the sensor unit 10. More specifically, the sensor 11 is disposed on the bottom surface of the sensor unit 10.

The analog information obtained by the sensor 11 is sent to the processor 21.

{Processor}

Referring back to FIGS. 1 through 3, the processor 21 is disposed close to the sensor 11 with respect to a central portion C1 of the oral measurement apparatus 1A in the longitudinal direction D1. More specifically, the processor 21 is disposed within the probe unit 20.

The processor 21 is configured to convert the analog information obtained by the sensor 11 into digital information. The processor 21 also outputs the digital information as a processing result.

The processor 21 includes a frequency converter circuit that converts information indicating the electrostatic capacity obtained by the sensor 11 into the frequency.

For example, the processor 21 repeatedly charges and discharges the sensor 11 that has obtained information indicating the electrostatic capacity, and converts this information into the frequency of the charge/discharge cycle determined by the charge/discharge speed.

In this manner, the processor 21 is configured to convert analog information indicating the electrostatic capacity in the mouth obtained from the sensor 11 into digital information indicating the frequency. The digital information obtained by the processor 21 is sent to the calculator 31 as the processing result. In the first embodiment, the conversion processing result generated by the processor 21 is the frequency.

In general, the processor 21 can be implemented by a semiconductor device, for example. The processor 21 can comprise a microcontroller, a central processing unit (CPU), a micro-processing unit (MPU), a graphics processing unit (GPU), a digital signal processor (DSP), a field-programmable gate array (FPGA), an application-specific integrated circuit (ASIC), a discrete semiconductor, or a large scale integration (LSI) circuit. The functions of the processor 21 may be implemented only by hardware or a combination of hardware and software. The processor 21 reads data and a program stored in a storage (not shown) within the processor 21 and executes various operations so as to implement a certain function, such as the algorithms described herein. The storage is implemented by a hard disk drive (HDD), a solid-state drive (SSD), a random access memory (RAM), a dynamic random access memory (DRAM), a ferroelectric memory, a flash memory, a magnetic disk, or a combination thereof, for example.

{Temperature Information Obtaining Section}

The temperature information obtaining section 22 obtains temperature information concerning the processor 21 and also outputs the temperature information. The temperature information concerning the processor 21 is information used for correcting information indicating the processing result generated by the processor 21. The temperature information concerning the processor 21 includes information indicating the temperature at which the sensor 11 has started obtaining analog information and that at which the sensor 11 has finished obtaining the analog information.

For example, the temperature information obtaining section 22 is configured to measure the electrical resistance of the processor 21 as information related to the temperature of the processor 21, and calculates the temperature information concerning the processor 21 based on information indicating the measured electrical resistance.

The temperature information obtaining section 22 includes a temperature-related information obtainer and a temperature information calculator. The temperature-related information obtainer is configured to obtain information related to the temperature of the processor 21. The temperature information calculator calculates temperature information concerning the processor 21 based on the temperature-related information obtained by the temperature-related information obtainer.

According to exemplary aspects, the temperature-related information obtainer can be, for example, a thermistor, a platinum electrode, or a thermocouple. In the first embodiment, the temperature information obtaining section 22 uses a thermistor. The temperature information obtaining section 22 measures the electrical resistance as the information related to the temperature of the processor 21 and calculates the temperature of the processor 21 based on the measured electrical resistance. In other words, the temperature information obtaining section 22 obtains information indicating the electrical resistance by using the temperature-related information obtainer, and calculates the temperature information concerning the processor 21, based on the information indicating the electrical resistance, by using the temperature information calculator.

The temperature information obtaining section 22 is configured to perform temperature measurements multiple times. That is, the temperature information obtaining section 22 obtains plural items of temperature information. For example, the temperature information obtaining section 22 obtains temperature information concerning the processor 21 when the sensor 11 has started obtaining information inside the mouth, that is, when the sensor 11 is brought into contact with the inside of the mouth. The temperature information obtaining section 22 also obtains temperature information concerning the processor 21 when the sensor 11 has finished obtaining information inside the mouth. Based on these plural items of temperature information, the temperature information obtaining section 22 determines temperature information used for correcting information indicating the processing result of the processor 21. For example, the average or the median of the plural items of temperature information can be used for correcting the processing result.

In this manner, in the temperature information obtaining section 22, the temperature-related information obtainer obtains analog information, and the temperature information calculator converts the analog information into digital information. More specifically, the temperature information obtaining section 22 converts information indicating the electrical resistance, which is analog information, into temperature information, which is digital information.

The temperature information obtained by the temperature information obtaining section 22 is output to the correction processor 32. In the first embodiment, the temperature information obtained by the temperature information obtaining section 22 is sent to the correction processor 32 via the processor 21. Alternatively, the temperature information may be directly sent to the correction processor 32 without via the processor 21. In other words, sending of temperature information by the temperature information obtaining section 22 includes sending of the temperature information to the correction processor 32 via the processor 21 and sending of the temperature information directly to the correction processor 32 without via the processor 21.

Figure 5:
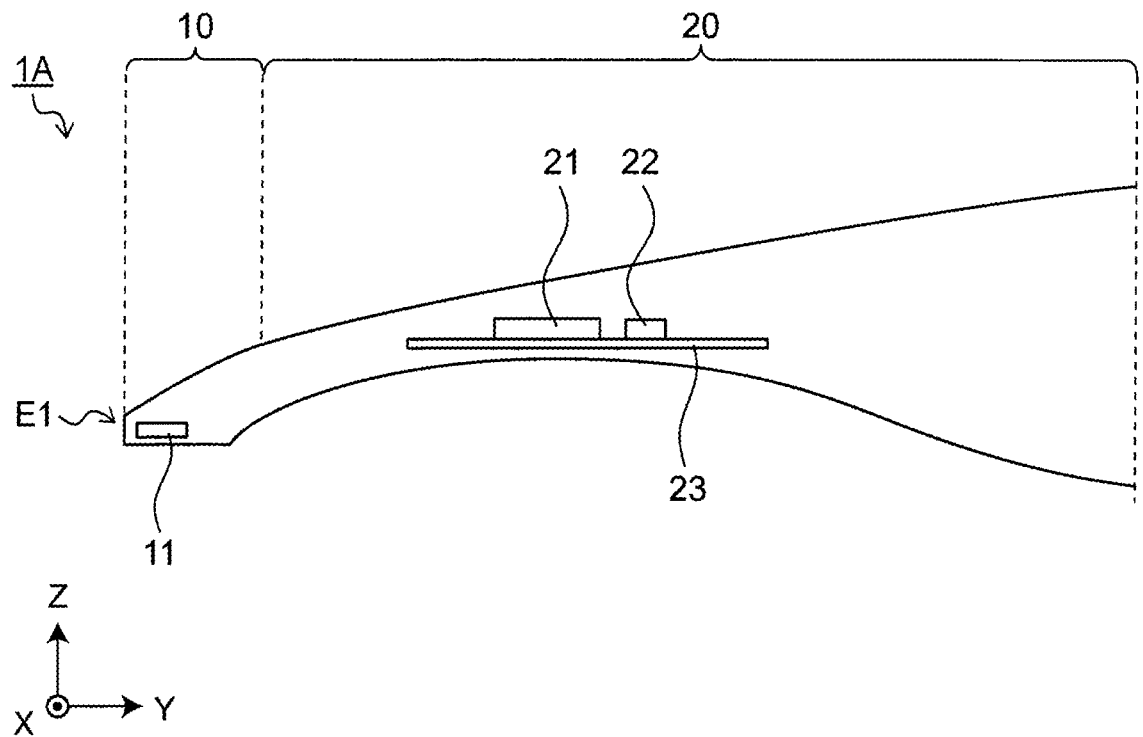
FIG. 5 is a schematic enlarged view illustrating the internal configuration of part of the oral measurement apparatus according to the first exemplary embodiment.

FIG. 5 is a schematic enlarged view illustrating the internal configuration of part of the oral measurement apparatus 1A according to the first embodiment. As shown in FIG. 5, the processor 21 and the temperature information obtaining section 22 are mounted on the substrate 23 and are disposed within the probe unit 20.

As shown, the temperature information obtaining section 22 is farther away from the first end E1 of the oral measurement apparatus 1A in the longitudinal direction D1 than the processor 21. In other words, the temperature information obtaining section 22 is located closer to the second end E2 of the oral measurement apparatus 1A in the longitudinal direction D1 than the processor 21 is. Analog information is sent from the sensor 11 to the processor 21. By avoiding the temperature information obtaining section 22 from intervening between the sensor 11 and the processor 21, the occurrence of noise can be reduced.

The temperature information obtaining section 22 is implemented by a semiconductor device, such as a microcontroller. The functions of the temperature information obtaining section 22 may be implemented only by hardware or a combination of hardware and software. The temperature information obtaining section 22 reads data and a program stored in a storage (not shown) within the processor 21 and executes various operations (e.g., the algorithms disclosed herein) so as to implement a certain function.

{Substrate}

The substrate 23 is used for mounting the processor 21 and the temperature information obtaining section 22 thereon. In the first embodiment, the substrate 23 serves as a heat transfer member which transfers the temperature of the processor 21 to the temperature information obtaining section 22.

Figure 6:
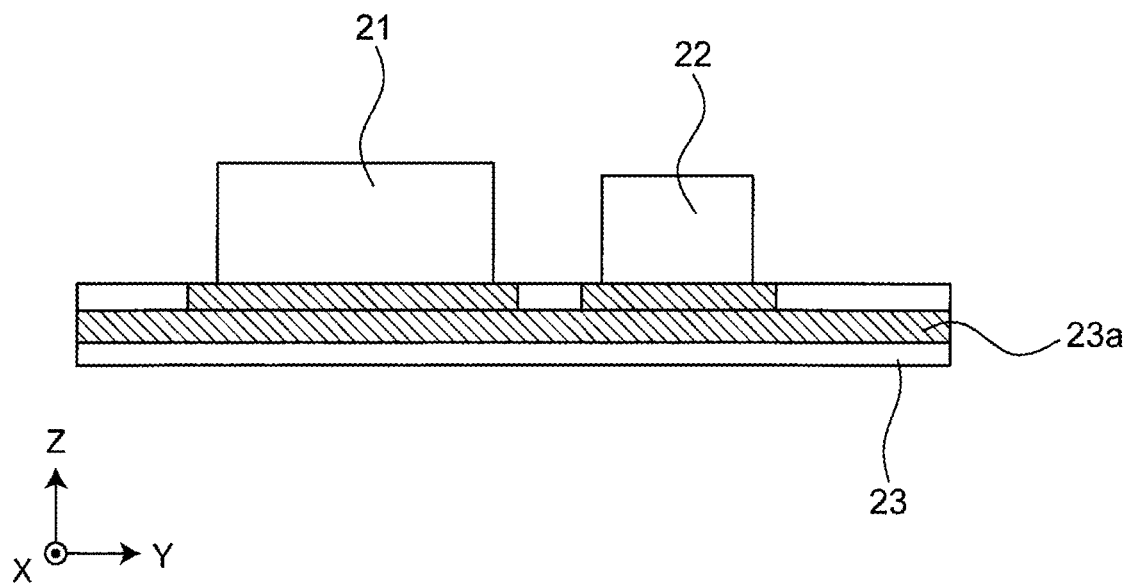
FIG. 6 is a schematic view illustrating an example in which a substrate is used as a heat transfer member.

FIG. 6 is a schematic view illustrating an example in which the substrate 23 is used as a heat transfer member. As shown in FIG. 6, the substrate 23 includes a ground pattern 23a. The ground pattern 23a can be formed by a copper foil pattern. The ground pattern 23a serves to connect the processor 21 to the temperature information obtaining section 22. That is, the processor 21 and the temperature information obtaining section 22 contact each other via the ground pattern 23a of the substrate 23. With this configuration, the ground pattern 23a can serve as a heat transfer member so as to transfer the heat of the processor 21 to the temperature information obtaining section 22 via the ground pattern 23a.

In this manner, the ground pattern 23a of the substrate 23 is used as a heat transfer member which transfers the heat of the processor 21 to the temperature information obtaining section 22.

{Calculator}

Referring back to FIGS. 1 through 3, the calculator 31 is configured to calculate the amount of moisture based on the processing result output from the processor 21, and more specifically, the frequency information output from the processor 21. The calculator 31 includes a moisture calculator circuit, for example, which calculates the amount of moisture based on a change in the frequency. A change in the frequency corresponds to the difference between the reference frequency and the frequency converted from the electrostatic capacity by the processor 21. The reference frequency is the frequency in the normal air atmosphere.

The information concerning the amount of moisture calculated by the calculator 31 is sent to the correction processor 32.

The calculator 31 is disposed within the holding portion 30.

{Correction Processor}

The correction processor 32 corrects the amount of moisture based on moisture amount information and temperature information.

For example, the correction processor 32 first calculates a correction amount based on the temperature information and a correction coefficient K. In an exemplary aspect, the correction coefficient K has been calculated before the oral measurement apparatus 1A starts measuring the amount of moisture. For example, the correction coefficient K may be calculated at the time of the manufacturing of the oral measurement apparatus 1A. Calculation of the correction coefficient K will be discussed later.

For example, the correction processor 32 adds the calculated correction amount to the amount of moisture calculated by the calculator 31, thereby correcting the amount of moisture.

Information indicating the amount of moisture corrected by the correction processor 32 is sent to the operation display unit 33.

The correction processor 32 is disposed within the holding portion 30.

The correction processor 32 can be implemented by a semiconductor device, such as a microcontroller, a CPU, an MPU, a GPU, a DSP, an FPGA, and an ASIC. The functions of the correction processor 32 can be implemented only by hardware or a combination of hardware and software. In operation, the correction processor 32 is configured to read data and a program stored in a storage (not shown) within the correction processor 32 and execute various operations so as to implement a certain function, such as the algorithms described herein. The storage is implemented by an HDD, an SSD, a RAM, a DRAM, a ferroelectric memory, a flash memory, a magnetic disk, or a combination thereof, for example.

Figure 7:
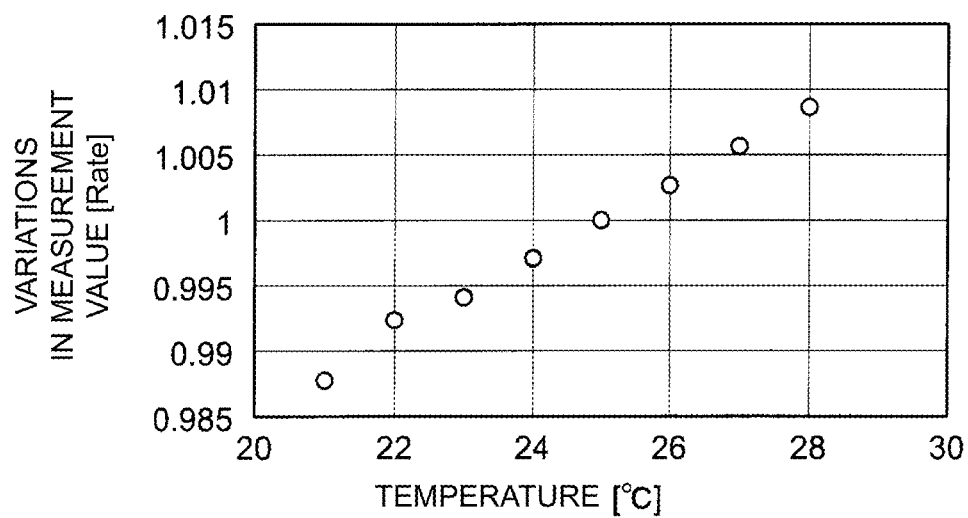
FIG. 7 is a graph illustrating an example of variations in the measurement value of the amount of moisture which has not been corrected.

Variations in the measurement value due to a change in the temperature of the processor 21 will be explained below. FIG. 7 is a graph illustrating an example of variations in the measurement value of the amount of moisture which has not been corrected. In FIG. 7, the horizontal axis indicates the temperature of the processor 21, while the vertical axis indicates variations in the measurement value. Variations in the measurement value refer to variations in the processing result obtained by the processor 21. In FIG. 7, the variations in the measurement value are represented by a variation rate with respect to the reference value "1", which is the value when the temperature of the processor 21 is 25° C.

FIG. 7 shows that a change in the temperature of the processor 21 causes variations in the measurement value. That is, a change in the temperature of the processor 21 influences the processing result of the processor 21. This may make it difficult to conduct high-accuracy measurements inside the mouth.

Figure 8:
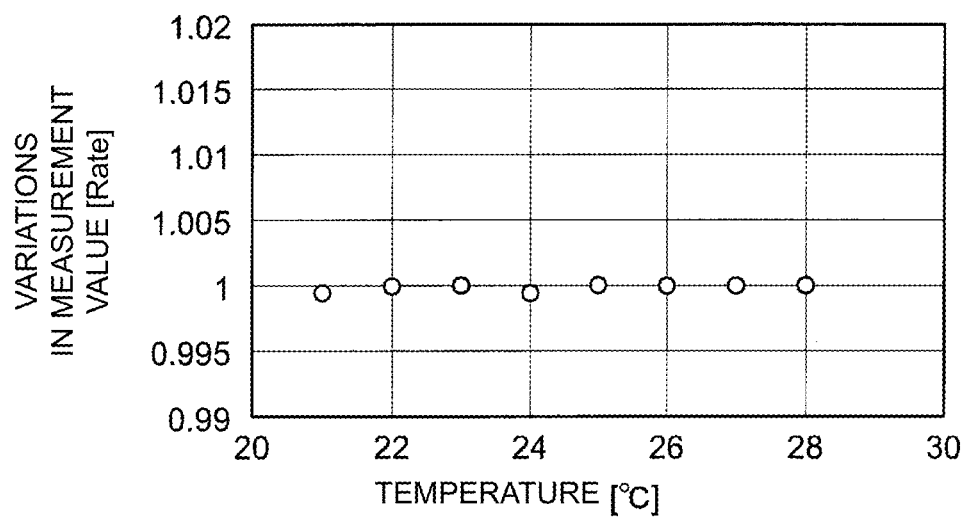
FIG. 8 is a graph illustrating an example of variations in the measurement value of the amount of moisture which has been corrected.

To deal with this issue, the correction processor 32 corrects the amount of moisture calculated by the calculator 31 based on the temperature information concerning the processor 21. FIG. 8 is a graph illustrating an example of variations in the measurement value of the amount of moisture which has been corrected. In FIG. 8, as well as in FIG. 7, the horizontal axis indicates the temperature of the processor 21, while the vertical axis indicates variations in the measurement value. FIG. 8 shows that variations in the measurement value in the oral measurement apparatus 1A are reduced as a result of the correction processor 32 correcting the calculated amount of moisture. This makes it possible to measure the amount of moisture in the mouth with high accuracy even when the temperature of the processor 21 is changed.

{Operation Display Unit}

The operation display unit 33 receives input from a user and also displays information indicating the amount of moisture corrected by the correction processor 32. The operation display unit 33 includes an operation unit that receives an operation performed by a user and a display that displays information.

The operation unit has one or more buttons which receive input from a user. One of the multiple buttons is a power button. Operating the power button can switch between the ON/OFF states of the oral measurement apparatus 1A. That is, when the oral measurement apparatus 1A in ON, it is ready to perform measurements.

The display of the operation display unit 33 displays information indicating the amount of moisture corrected by the correction processor 32.

The operation display unit 33 is disposed on the top surface of the holding portion 30.

In the exemplary aspect, the oral measurement apparatus 1A includes a controller that centrally controls the elements forming the oral measurement apparatus 1A. The controller includes a memory in which programs are stored and a processing circuit corresponding to a processor, such as a CPU. The controller executes a program stored in the memory, for example. In the first embodiment, the controller controls the sensor 11, the processor 21, the temperature information obtaining section 22, the substrate 23, the calculator 31, the correction processor 32, and the operation display unit 33.

[Calculation of Correction Coefficient]

Figure 9:
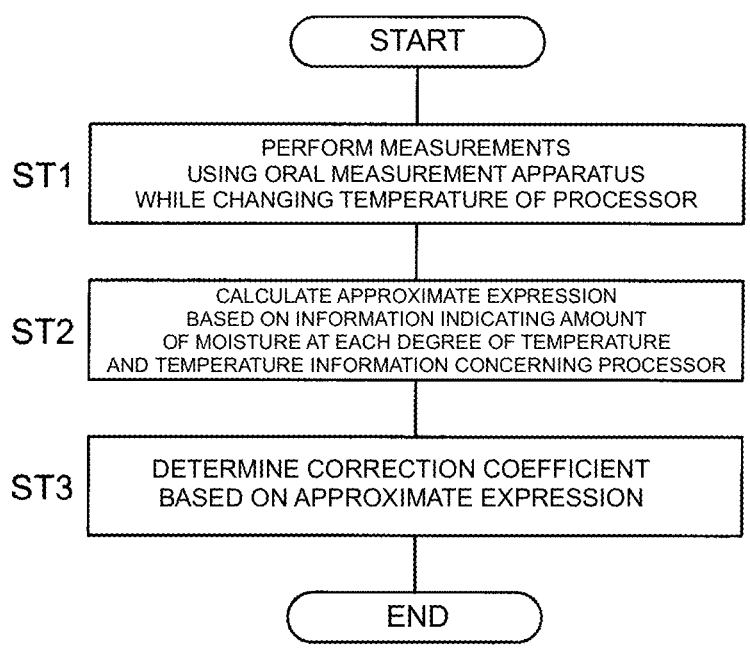
FIG. 9 is a flowchart illustrating an example of the approach to calculating a correction coefficient used in the oral measurement apparatus according to the first exemplary embodiment.

An example of the approach to calculating the correction coefficient K used for correction processing executed by the correction processor 32 will be described below with reference to FIG. 9. FIG. 9 is a flowchart illustrating an example of the approach to calculating the correction coefficient K used in the oral measurement apparatus 1A according to the first embodiment.

In step ST1, the oral measurement apparatus 1A performs measurements by changing the temperature of the processor 21. More specifically, a subject to be measured is brought into contact with the sensor 11 and is kept under a predetermined condition, and in this state, the temperature of the processor 21 is changed step by step. The oral measurement apparatus 1A performs measurements every time the temperature of the processor 21 is changed. The above-described predetermined condition is that the moisture of the subject contacting the sensor 11 is maintained at a certain amount. The temperature of the processor 21 is changed by using a heating device, such as a heater.

In step ST1, the temperature of the processor 21 is changed between 21 to 28° C. by each degree. The processor 21 processes analog information which is obtained by the sensor 11 at each degree of the temperature.

In the first embodiment, the processor 21 converts the electrostatic capacity obtained by the sensor 11 into the frequency. In step ST1, while the temperature of the processor 21 is changed by each degree, the processor 21 converts the electrostatic capacity into the frequency. As the processing results of the processor 21, temperature information concerning the processor 21 and information indicating the frequency (e.g., a measurement value) corresponding to each degree of the temperature of the processor 21 can be obtained.

The processing results of the processor 21 are sent to the calculator 31 and the correction processor 32. More specifically, the temperature information indicating the multiple degrees of the temperature of the processor 21 is sent to the correction processor 32, while the frequency information indicating the frequencies corresponding to the multiple degrees of the temperature of the processor 21 is sent to the calculator 31.

Based on the information indicating the frequency corresponding to each degree of the temperature, the calculator 31 calculates the amount of moisture corresponding to each degree of the temperature. The calculator 31 sends information indicating the calculated amounts of moisture to the correction processor 32.

In step ST2, an approximate expression is calculated based on the information indicating the amount of moisture corresponding to each degree of the temperature, the processing results of the processor 21, and the temperature information concerning the processor 21. More specifically, the correction processor 32 calculates the approximate expression based on the information concerning the temperature of the processor 21 varied in step ST1 and the information indicating the amount of moisture (e.g., a measurement value) corresponding to each degree of the temperature obtained in step ST1. The approximate expression may be calculated by the following expression, for example:

$$M = a \times T + b$$

where M is the amount of moisture (e.g., a measurement value), T is the temperature of the processor 21, and a and b are given numerical values.

In step ST3, the correction coefficient K is determined based on the approximate expression calculated in step ST2. For example, the correction processor 32 sets "a", which is the slope of the above-described approximate expression, as the correction coefficient K. The correction processor 32 stores the determined correction coefficient K in a storage.

As a result of executing steps ST1 through ST3, the correction coefficient K can be calculated. The approximate expression calculated in step ST2 is only an example and is not restricted thereto. The approximate expression may be a linear expression or a polynomial expression.

[Operation of Oral Measurement Apparatus]

Figure 10:
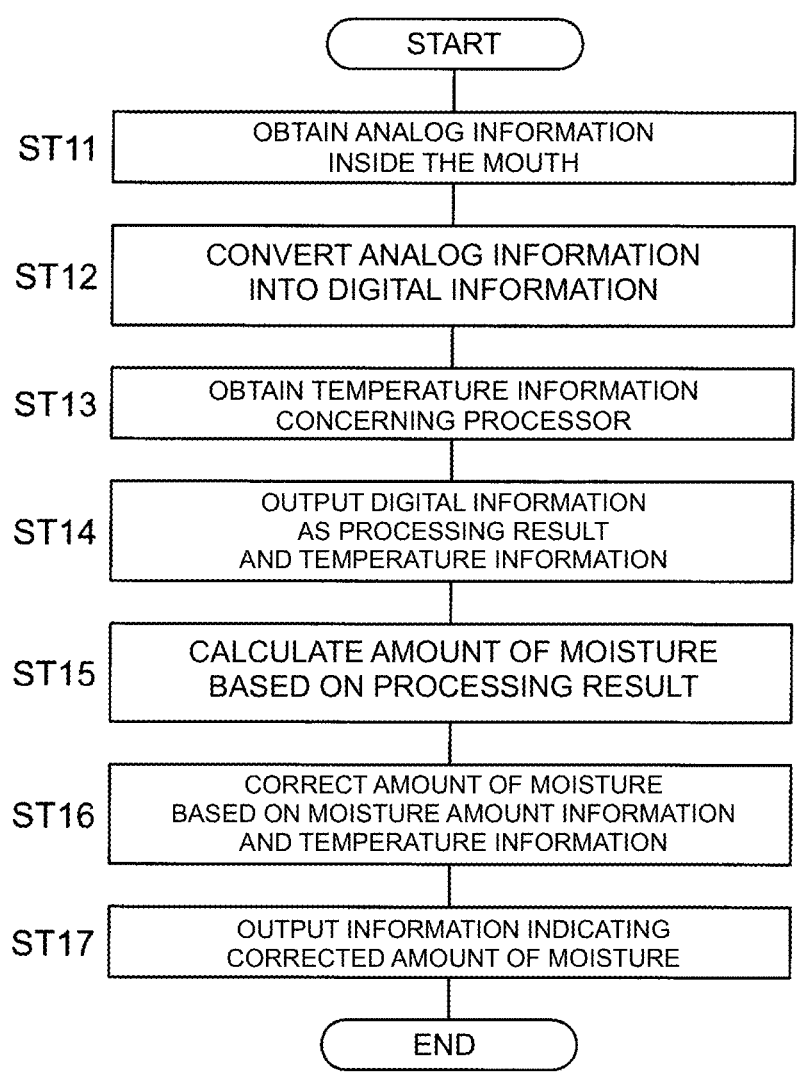
FIG. 10 is a flowchart illustrating an example of the operation of the oral measurement apparatus according to the first exemplary embodiment.
Figure 11:
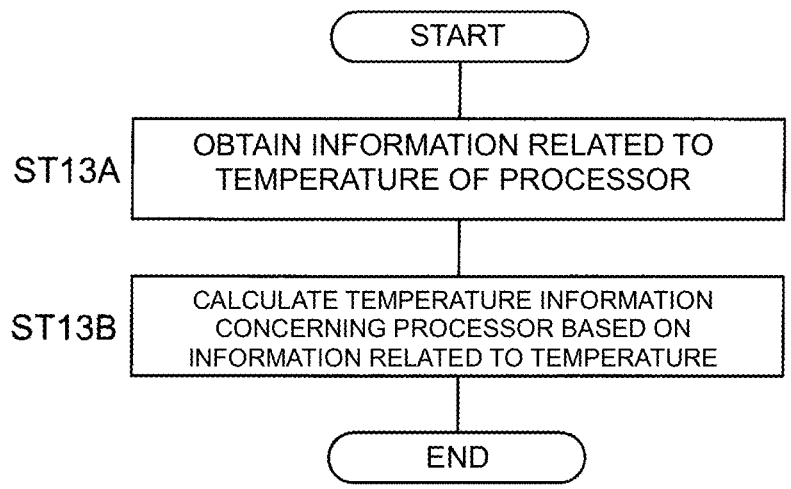
FIG. 11 is a flowchart illustrating an example of the approach to obtaining temperature information.
Figure 12:
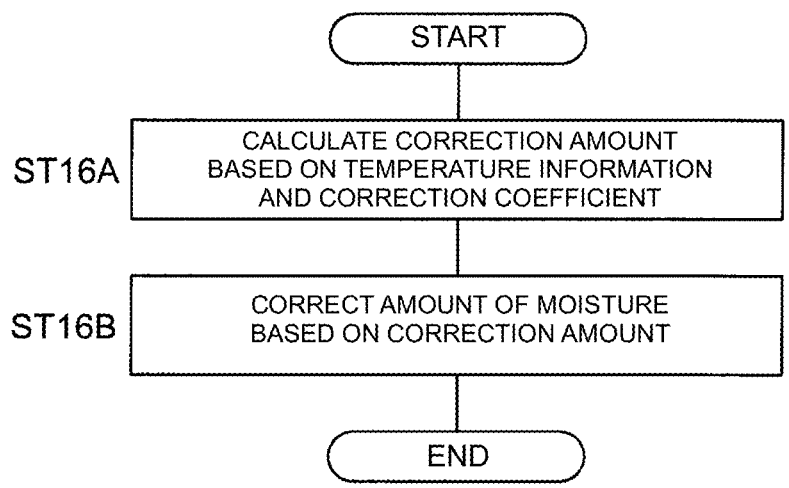
FIG. 12 is a flowchart illustrating an example of the approach to correcting a measurement result.

An example of the operation of the oral measurement apparatus 1A, that is, an example of a method for measuring the amount of moisture in the mouth, will be described below with reference to FIGS. 10 through 12. FIG. 10 is a flowchart illustrating an example of the operation of the oral measurement apparatus 1A according to the first embodiment. FIG. 11 is a flowchart illustrating an example of the approach to obtaining temperature information. FIG. 12 is a flowchart illustrating an example of the approach to correcting a measurement result.

Reference will first be made to FIG. 10. In step ST11, analog information inside the mouth is obtained by the sensor 11. More specifically, the sensor 11 is brought into contact with the inside of the mouth of a user so as to obtain analog information inside the mouth. The analog information obtained by the sensor 11 is sent to the processor 21, which is communicatively coupled thereto.

In the first embodiment, the sensor 11 is a capacitive sensor and thus obtains information indicating the electrostatic capacity as the analog information.

In step ST12, the processor 21 converts the analog information obtained by the sensor 11 into digital information. In the first embodiment, the processor 21 converts the information indicating the electrostatic capacity obtained by the sensor 11 into the frequency. In this manner, the processor 21 converts analog information indicating the electrostatic capacity obtained by the sensor 11 into digital information indicating the frequency.

In step ST13, the temperature information obtaining section 22 obtains temperature information concerning the processor 21. More specifically, in step ST13, the temperature information obtaining section 22 obtains the temperature of the processor 21 at the start of the measurements and that before the start of the measurements. The temperature information obtaining section 22 then calculates the average of the obtained temperatures.

Step ST13, namely, the processing for calculating the temperature of the processor 21 by the temperature information obtaining section 22, will be discussed in detail with reference to FIG. 11. FIG. 11 is a flowchart illustrating processing executed at the start of the measurements and at the end of the measurements.

In step ST13A, the temperature-related information obtainer of the temperature information obtaining section 22 obtains information related to the temperature of the processor 21. In the first embodiment, the temperature-related information obtainer is a thermistor and thus obtains information indicating the electrical resistance of the processor 21 as the information related to the temperature of the processor 21.

In step ST13B, the temperature information calculator of the temperature information obtaining section 22 calculates temperature information concerning the processor 21, based on the temperature-related information obtained by the temperature-related information obtainer. In the first embodiment, the temperature information calculator calculates the temperature of the processor 21 based on the information indicating the electrical resistance of the processor 21 obtained by the temperature-related information obtainer.

In this manner, as a result of executing steps ST13A and ST13B, the temperature information obtaining section 22 obtains the temperature of the processor 21 at the start of the measurements and that at the end of the measurements.

Referring back to FIG. 10, in step ST13, the temperature information obtaining section 22 uses the average of the temperature at the start of the measurements and that before the start of the measurements as the temperature information concerning the processor 21.

In step ST14, the processor 21 outputs the processing result (e.g., frequency information) obtained by converting the analog information into the digital information, while the temperature information obtaining section 22 outputs the temperature information. In the first embodiment, the processor 21 sends the processing result to the calculator 31, while the temperature information obtaining section 22 sends the temperature information to the correction processor 32 via the processor 21.

In step ST15, the calculator 31 calculates the amount of moisture based on the processing result of the processor 21. In the first embodiment, the calculator 31 calculates a change in the frequency, based on the frequency converted from the electrostatic capacity by the processor 21. The calculator 31 then calculates the amount of moisture based on a change in the frequency, and sends information indicating the calculated amount of moisture to the correction processor 32.

In ST16, the correction processor 32 corrects the calculated amount of moisture based on the moisture amount information and the temperature information. In the first embodiment, the correction processor 32 corrects the amount of moisture calculated by the calculator 31, based on the temperature information concerning the processor 21 obtained by the temperature information obtaining section 22.

Step ST16, namely, the processing for correcting the processing result, will be discussed below in detail with reference to the flowchart of FIG. 12.

In step ST16A, the correction processor 32 calculates a correction amount based on the temperature information concerning the processor 21 and the correction coefficient K. The correction processor 32 calculates the correction amount according to the following expression, for example:

$$Q = K \times (T1 - T0)$$

where Q is the correction amount, K is the correction coefficient, T1 is the temperature of the processor 21, and T0 is the reference temperature.

The correction coefficient K has been calculated before the start of the measurements (e.g., as a predetermined value) and is stored in the storage of the correction processor 32. The temperature T1 is based on the temperature information concerning the processor 21 obtained in step ST13. The reference temperature T0 is the temperature which serves as the reference and is set to be a given value. Moreover, the reference temperature T0 can be stored in the storage of the correction processor 32.

The correction processor 32 reads the correction coefficient K and the reference temperature T0 from the storage, and multiplies the difference between the temperature T1 of the processor 21 and the reference temperature T0 by the correction coefficient K, thereby calculating the correction amount Q.

The above-described expression for calculating the correction amount is only an example and is not restricted thereto.

In step ST16B, the correction processor 32 corrects the processing result of the processor 21 based on the calculated correction amount Q. For example, the correction processor 32 corrects the processing result of the processor 21 according to the following expression:

$$P = M + Q$$

where P is the corrected amount of moisture, M is the amount of moisture which has not been corrected (measurement value), and Q is the correction amount.

The correction processor 32 corrects the amount of moisture by adding the correction amount Q to the amount of moisture M which has not been corrected.

In general, it is noted that the above-described expression for correcting the amount of moisture is only an example and is not restricted thereto.

Information indicating the amount of moisture corrected by the correction processor 32 is sent to the operation display unit 33.

Referring back to FIG. 10, in step ST17, the operation display unit 33 displays the information indicating the corrected amount of moisture. The operation display unit 33 displays the corrected amount of moisture as a numerical value, a graph, or an indicator, for example.

As a result of executing steps ST11 through ST17, the amount of moisture can be corrected and displayed.

[Exemplary Use of the Oral Measurement Apparatus]

Figure 13:
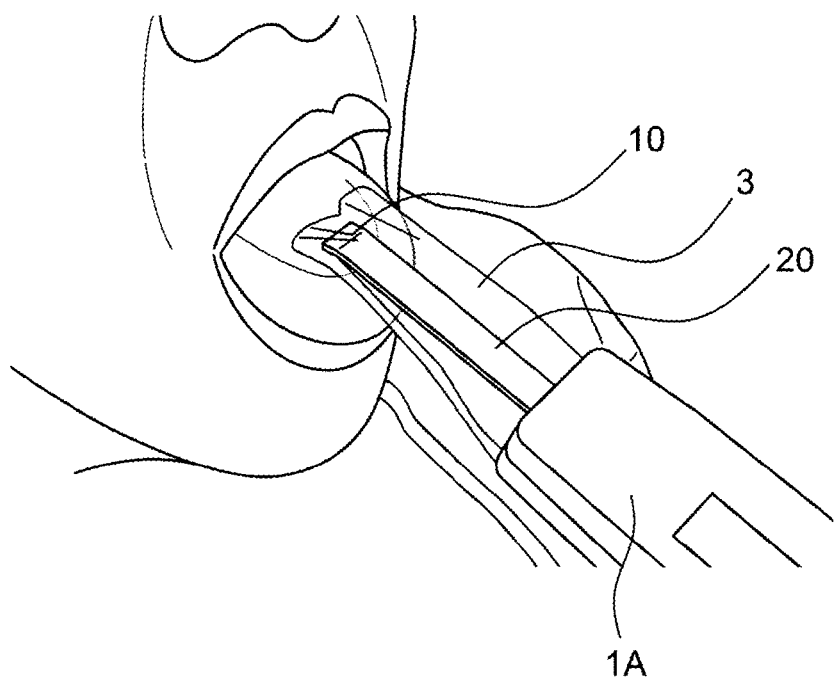
FIG. 13 is a schematic view illustrating an example of the oral measurement apparatus of the first exemplary embodiment in operation.

An example of the use of the oral measurement apparatus 1A will be discussed below with reference to FIG. 13. FIG. 13 is a schematic view illustrating an example in which the oral measurement apparatus 1A of the first embodiment is being used.

As shown in FIG. 13, the sensor unit 10 and the probe unit 20 of the oral measurement apparatus 1A are first covered by a film 3. The power button of the operation display unit 33 is pressed, and then, the oral measurement apparatus 1A is powered ON and is ready for use.

Measurements are conducted multiple times (e.g., three times) with the oral measurement apparatus 1A.

In each time of measurement, the sensor 11 provided on the bottom surface of the sensor unit 10 is brought into contact with the inside of the mouth of a user. For example, the sensor 11 is applied to the tongue of the user, and then, the measurement is started.

At the end of the measurement, the oral measurement apparatus 1A informs the user by sound, for example, that the measurement has finished.

The measurement is repeated in this manner three times, and then, the measurement result is displayed on the operation display unit 33.

The oral measurement apparatus 1A according to the first embodiment achieves the following advantages.

The oral measurement apparatus 1A includes the sensor 11, the processor 21, and the temperature information obtaining section 22. The sensor 11 is disposed at the first end E1 (e.g., one end) of the oral measurement apparatus 1A in the longitudinal direction D1 and obtains analog information inside a mouth. The processor 21 is disposed close to the sensor 11 with respect to the central portion C1 of the oral measurement apparatus 1A in the longitudinal direction D1. The processor 21 converts the analog information obtained by the sensor 11 into digital information and outputs the digital information as a processing result. The temperature information obtaining section 22 obtains temperature information concerning the processor 21 and outputs the temperature information.

With this configuration, the temperature information concerning the processor 21 can be obtained. Additionally, the oral measurement apparatus 1A outputs the obtained temperature information so that variations in the processing result caused by a change in the temperature of the processor 21 can be reduced. For example, the oral measurement apparatus 1A can output the temperature information to the correction processor 32. The correction processor 32 corrects the measurement result based on the temperature information.

In general, it should be appreciated that analog information obtained by the sensor 11 is vulnerable to noise. In the oral measurement apparatus 1A, the processor 21 is disposed close to the sensor 11 with respect to the central portion C1 of the oral measurement apparatus 1A in the longitudinal direction D1, thereby making it possible to reduce the occurrence of noise.

When the measurement is conducted, the sensor 11 touches the inside of a mouth. As the processor 21 is disposed closer to the sensor 11, heat in the mouth can be more easily transferred to the processor 21 and the temperature of the processor 21 is more likely to change. The oral measurement apparatus 1A can obtain temperature information concerning the processor 21 by using the temperature information obtaining section 22 and output information for correcting the processing result. Hence, high-accuracy measurements inside the mouth can be achieved.

The oral measurement apparatus 1A includes the casing 2 for storing the sensor 11, the processor 21, and the temperature information obtaining section 22 therein. The casing 2 includes the sensor unit 10, the probe unit 20, and the holding portion 30. The sensor unit 10 is disposed close to the first end E1 of the oral measurement apparatus 1A in the longitudinal direction D1. The probe unit 20 is formed in a bar-like shape and connects the sensor unit 10 and the holding portion 30 each other with the probe unit 20 interposed therebetween. The holding portion 30 is disposed close to the second end E2 of the oral measurement apparatus 1A in the longitudinal direction D1. The sensor 11 is disposed in or on the sensor unit 10. The processor 21 and the temperature information obtaining section 22 are disposed within the probe unit 20. This configuration makes it easier to bring the sensor 11 into contact with the inside of the mouth and also to obtain the temperature information concerning the processor 21 with high accuracy.

The temperature information obtaining section 22 is disposed closer to the second end E2 of the oral measurement apparatus 1A in the longitudinal direction D1 than the processor 21. This configuration can prevent the temperature information obtaining section 22 from intervening between the sensor 11 and the processor 21, thereby making it possible to reduce the occurrence of noise.

The processor 21 and the temperature information obtaining section 22 contact each other via the ground pattern 23a of the substrate 23, which serves as a heat transfer member. This configuration can enhance thermal coupling between the processor 21 and the temperature information obtaining section 22. The temperature information obtaining section 22 is thus able to obtain temperature information concerning the processor 21 with high accuracy.

The oral measurement apparatus 1A also includes the calculator 31 that calculates the amount of moisture based on the processing result output from the processor 21. With this configuration, the amount of moisture in the mouth can be calculated based on the processing result obtained by the processor 21.

The oral measurement apparatus 1A also includes the correction processor 32 that corrects the amount of moisture based on moisture amount information and temperature information. This configuration enables the correction processor 32 to correct the amount of moisture based on the temperature information concerning the processor 21, thereby making it possible to enhance the measurement accuracy.

In the first embodiment, the oral measurement apparatus 1A includes the sensor 11, the processor 21, the temperature information obtaining section 22, the substrate 23, the calculator 31, the correction processor 32, and the operation display unit 33. However, in alternative aspects, the oral measurement apparatus 1A is not restricted to this configuration. The above-described elements may be included together in one device or be distributed over plural devices. For example, the processor 21 and the temperature information obtaining section 22 may be formed integrally. The sensor 11 and the processor 21 may be formed integrally. The calculator 31 and the correction processor 32 may be formed integrally.

In the first embodiment, the calculator 31, the correction processor 32, and the operation display unit 33 are disposed in the oral measurement apparatus 1A. This configuration is only an example. The calculator 31, the correction processor 32, and the operation display unit 33 may not necessarily be disposed in the oral measurement apparatus 1A, and instead, they may be disposed in a processing device different from the oral measurement apparatus 1A.

In the first embodiment, the subject to be measured by the oral measurement apparatus 1A is the amount of moisture, but it is not limited thereto. The oral measurement apparatus 1A may measure any subject as long as it can determine the state inside the mouth. For example, the oral measurement apparatus 1A may measure the secretion of saliva, bit force, tongue pressure, tongue color, and/or amounts of various substances contained in saliva in various alternative aspects. More specifically, the oral measurement apparatus 1A may measure the secreted amounts of electrolytes, various enzymes, proteins, and ammonia as the subjects to be measured. In this case, the calculator 31 calculates the amounts of these substances.

In the first embodiment, the casing 2 includes the sensor unit 10, the probe unit 20, and the holding portion 30. The casing 2 may be however configured in any manner as long as it extends in the longitudinal direction.

In the first embodiment, the sensor 11 is a capacitive sensor, but it is not limited thereto. The sensor 11 may be any type of sensor that can obtain analog information inside the mouth. For example, the sensor 11 may be at least one of an impedance measuring sensor, an optical sensor, a load sensor, and a humidity sensor.

In the first embodiment, the processor 21 converts the electrostatic capacity into the frequency. However, as long as the processor 21 includes a circuit that converts analog information obtained by the sensor 11 into digital information, the type of information subjected to conversion processing is not limited to the above-described information. The processor 21 may also include another processing circuit.

In the first embodiment, the calculator 31 is disposed within the holding portion 30. The calculator 31 may alternatively be disposed within the probe unit 20. In this case, the calculator 31 and the processor 21 may be formed integrally. For example, the processor 21 may include a frequency converter circuit that converts information indicating the electrostatic capacity into information indicating the frequency and a moisture amount calculator circuit that calculates the amount of moisture based on a change in the frequency.

In the first embodiment, the temperature information obtaining section 22 includes the temperature-related information obtainer and the temperature information calculator. It is noted that this configuration is only an example. The temperature information obtaining section 22 may not necessarily include the temperature information calculator. In this case, the temperature information calculator may be provided in the processor 21, the calculator 31, or the correction processor 32, for example.

Although in the first embodiment the temperature-related information obtainer is a thermistor, it is not limited thereto. The temperature-related information obtainer may be another type of element that can obtain temperature-related information used for calculating temperature information concerning the processor 21. The temperature-related information obtainer may be an infrared sensor, for example, in an alternative aspect.

In the first embodiment, the temperature information obtaining section 22 calculates temperature information concerning the processor 21 based on temperature-related information. This configuration is only an example. The temperature information obtaining section 22 may not necessarily obtain temperature-related information if it is able to obtain temperature information concerning the processor 21.

In the first embodiment, the temperature information obtaining section 22 obtains temperature information concerning the processor 21 at the start of the measurements and that at the end of the measurements. However, the timing at which temperature information concerning the processor 21 is obtained is not limited to these timings if multiple items of temperature information are obtained. For example, the temperature information obtaining section 22 may obtain temperature information before the measurements and that during the measurements and/or that after the measurements.

In the first embodiment, the processor 21 and the temperature information obtaining section 22 are mounted on the substrate 23. However, the provision of the substrate 23 may be omitted in an alternative aspect.

In the first embodiment, the ground pattern 23a of the substrate 23 is used as a heat transfer member that connects the processor 21 and the temperature information obtaining section 22 with each other via the ground pattern 23a. This is only an example, and another type of heat transfer member may be used as long as the processor 21 and the temperature information obtaining section 22 contact each other via this heat transfer member. For example, a member other than the substrate 23 may be used as a heat transfer member. Alternatively, a portion of the substrate 23 other than the ground pattern 23a may be used as a heat transfer member.

Although in the first embodiment the correction coefficient K is calculated at the time of the manufacturing of the oral measurement apparatus 1A, it may be calculated at another time if it is calculated before the start of the measurements.

In the first embodiment, the correction processor 32 calculates the calculation amount by using the correction coefficient K. The correction processor 32 may however use another factor that makes it possible to calculate the correction amount based on temperature information concerning the processor 21. For example, a table indicating the relationship between the temperature of the processor 21 and the correction amount may be used in alternative aspects.

Although in the first embodiment the measurements are conducted multiple times, the measurement may be performed only once.

Second Exemplary Embodiment

An oral measurement apparatus according to a second embodiment will be described below. The second embodiment will be explained mainly by referring to points different from the first embodiment. In the second embodiment, the elements identical to or similar to those of the first embodiment will be designated by like reference numerals, and a description given in the first embodiment will be omitted.

Figure 14:
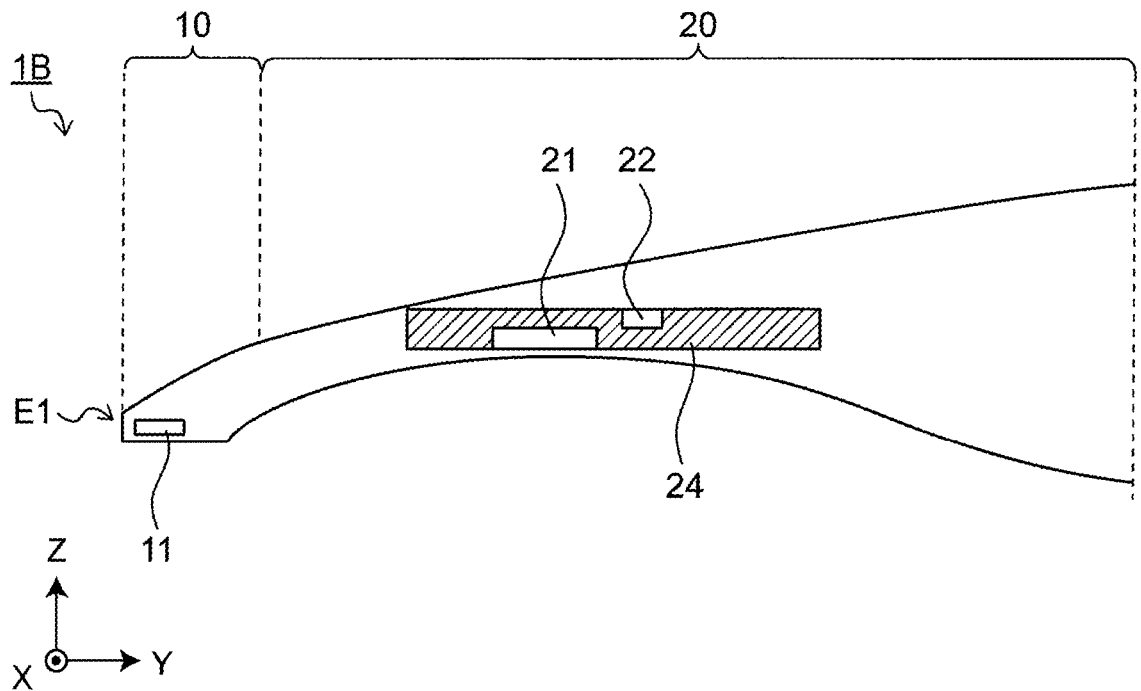
FIG. 14 is a schematic enlarged view illustrating part of the internal configuration of an oral measurement apparatus according to a second exemplary embodiment.

An example of an oral measurement apparatus according to the second embodiment will be described below with reference to FIG. 14. FIG. 14 is a schematic enlarged view illustrating the internal configuration of part of an oral measurement apparatus 1B according to the second embodiment.

The second embodiment is different from the first embodiment in that the substrate 23 is omitted and a different heat transfer member 24 is provided.

As shown in FIG. 14, the oral measurement apparatus 1B includes the heat transfer member 24 that connects the processor 21 and the temperature information obtaining section 22 with each other via the heat transfer member 24. The heat transfer member 24 is made of a material having a high thermal conductivity, such as a metal member, silicone, or carbon, for example. As the metal member, an aluminum member may be used, for example.

The heat transfer member 24 is formed in a block-like shape and covers at least part of each of the processor 21 and the temperature information obtaining section 22. In other words, each of the processor 21 and the temperature information obtaining section 22 is at least partially embedded in the heat transfer member 24. In the second embodiment, the processor 21 is embedded in the heat transfer member 24, except for the bottom surface, while the temperature information obtaining section 22 is embedded in the heat transfer member 24, except for the top surface.

The oral measurement apparatus 1B according to the second embodiment achieves the following advantages.

The oral measurement apparatus 1B includes the heat transfer member 24 that connects the processor 21 and the temperature information obtaining section 22 via the heat transfer member 24. The heat transfer member 24 is made of a metal, silicone, or carbon, for example. This configuration can enhance thermal coupling between the processor 21 and the temperature information obtaining section 22.

Each of the processor 21 and the temperature information obtaining section 22 is at least partially embedded in the heat transfer member 24. In other words, the heat transfer member 24 covers at least part of each of the processor 21 and the temperature information obtaining section 22. With this configuration, the contact area between the heat transfer member 24 and each of the processor 21 and the temperature information obtaining section 22 can be increased. This facilitates the transferring of heat of the processor 21 to the temperature information obtaining section 22. The temperature information obtaining section 22 is thus able to obtain temperature information concerning the processor 21 with even higher accuracy.

In the second embodiment, the heat transfer member 24 is formed in a block-like shape, but this is only an example. The heat transfer member 24 may be formed in any shape in which the processor 21 and the temperature information obtaining section 22 are connected with each other via the heat transfer member 24.

As shown in the second embodiment, the processor 21 is embedded in the heat transfer member 24, except for the bottom surface, while the temperature information obtaining section 22 is embedded in the heat transfer member 24, except for the top surface. The processor 21 and the temperature information obtaining section 22 may be provided in the heat transfer member 24 in any manner as long as they contact the heat transfer member 24. For example, each of the processor 21 and the temperature information obtaining section 22 may be entirely embedded in the heat transfer member 24, or may be at least partially disposed in or on the heat transfer member 24.

Although in the second embodiment the oral measurement apparatus 1B does not include a substrate for mounting the processor 21 and the temperature information obtaining section 22 thereon, it may include such a substrate in a variation of the exemplary aspect.

Third Exemplary Embodiment

An oral measurement apparatus according to a third embodiment will be described below. The third embodiment will be explained mainly by referring to points different from the first embodiment. In the third embodiment, the elements identical to or similar to those of the first embodiment will be designated by like reference numerals, and a description given in the first embodiment will be omitted.

Figure 15:
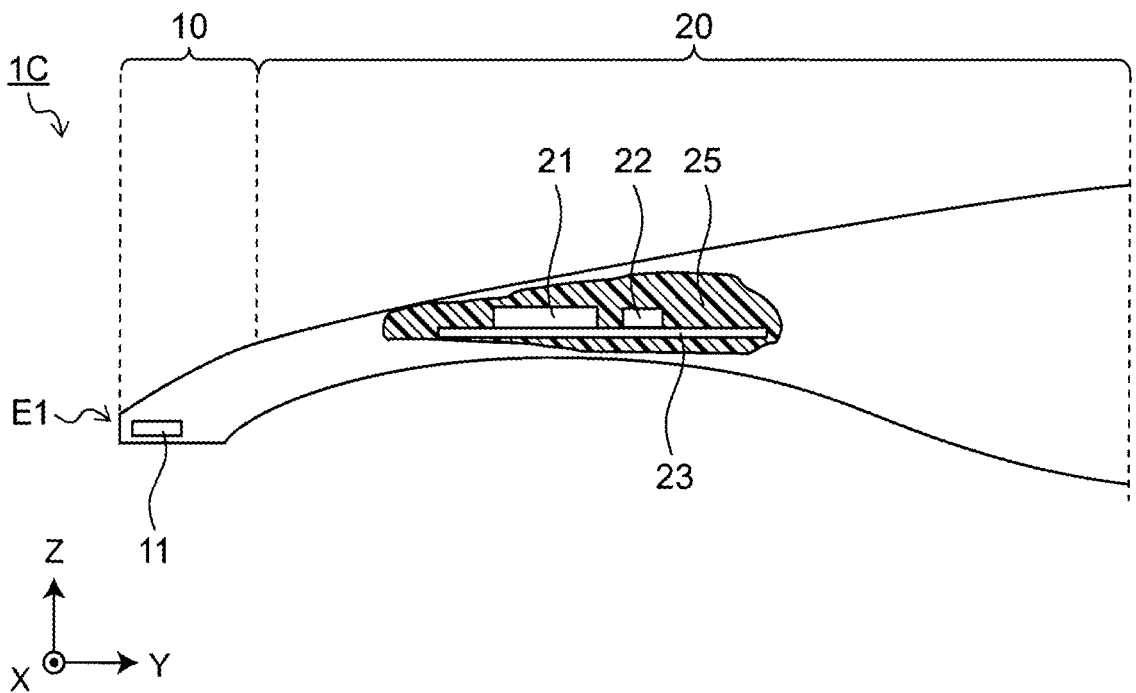
FIG. 15 is a schematic enlarged view illustrating part of the internal configuration of an oral measurement apparatus according to a third exemplary embodiment.

An example of an oral measurement apparatus according to the third embodiment will be described below with reference to FIG. 15. FIG. 15 is a schematic enlarged view illustrating the internal configuration of part of an oral measurement apparatus 1C according to the third embodiment.

The third embodiment is different from the first embodiment in that the processor 21 and the temperature information obtaining section 22 are sealed with a heat transfer resin member 25.

As shown in FIG. 15, in the oral measurement apparatus 1C, the processor 21 and the temperature information obtaining section 22 are sealed with the heat transfer resin member 25. The heat transfer resin member 25 is made of a resin material, such as PC, PBT, epoxy resin, or silicone.

The oral measurement apparatus 1C according to the third embodiment achieves the following advantages.

In the oral measurement apparatus 1C, the processor 21 and the temperature information obtaining section 22 are sealed with the heat transfer resin member 25. This configuration can enhance thermal coupling between the processor 21 and the temperature information obtaining section 22. The heat transfer resin member 25 can also protect the processor 21 and the temperature information obtaining section 22. For example, even if an external load is applied to the oral measurement apparatus 1C, the processor 21 and the temperature information obtaining section 22 can be protected by the heat transfer resin member 25 from damage.

Fourth Exemplary Embodiment

An oral measurement system according to a fourth embodiment will be described below. The fourth embodiment will be explained mainly by referring to points different from the first embodiment. In the fourth embodiment, the elements identical to or similar to those of the first embodiment will be designated by like reference numerals, and a description given in the first embodiment will be omitted.

Figure 16:
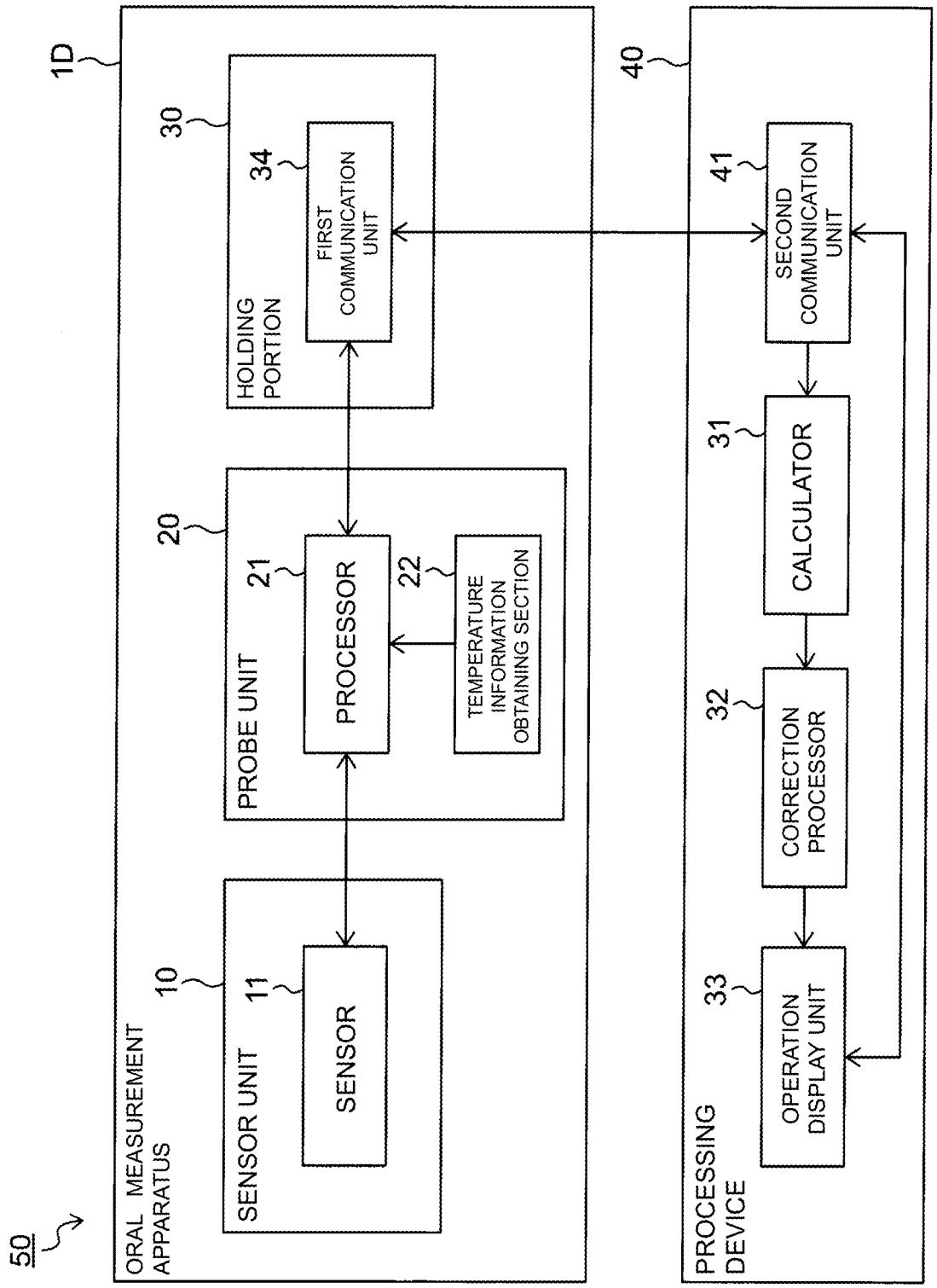
FIG. 16 is a block diagram illustrating an example of the schematic configuration of an oral measurement system according to a fourth exemplary embodiment.

An example of the oral measurement system according to the fourth embodiment will be described below with reference to FIG. 16. FIG. 16 is a block diagram illustrating an example of the schematic configuration of an oral measurement system 50 according to the fourth embodiment.

The fourth embodiment is different from the first embodiment in that information obtained by an oral measurement apparatus 1D is sent to a processing device 40 and the processing device 40 measures the amount of moisture.

As shown in FIG. 16, the oral measurement system 50 includes the oral measurement apparatus 1D and the processing device 40.

{Oral Measurement Apparatus}

The oral measurement apparatus 1D includes a sensor 11, a processor 21, a temperature information obtaining section 22, and a first communication unit 34. The sensor 11, the processor 21, and the temperature information obtaining section 22 are similar to those of the first embodiment, and a detailed explanation thereof will be omitted.

The first communication unit 34 communicates with the processing device 40. More specifically, the first communication unit 34 sends the processing result obtained by the processor 21 and temperature information to the processing device 40.

The first communication unit 34 includes a circuit for communicating with the processing device 40 in compliance with a predetermined communication standard. Examples of the predetermined communication standard are a local area network (LAN), Wi-Fi®, Bluetooth®, a universal serial bus (USB), a high-definition multimedia interface (HDMI), a controller area network (CAN), and a serial peripheral interface (SPI).

In the oral measurement apparatus 1D, the processor 21 converts analog information obtained by the sensor 11 into digital information and outputs the digital information as a processing result. In the fourth embodiment, the processor 21 converts the electrostatic capacity obtained by the sensor 11 into the frequency. The processor 21 sends the frequency information to the processing device 40 as the processing result via the first communication unit 34.

The temperature information obtaining section 22 obtains temperature information concerning the processor 21 and outputs the temperature information. In the fourth embodiment, the temperature information obtaining section 22 sends the temperature information to the processing device 40 via the processor 21 and the first communication unit 34.

The oral measurement apparatus 1D includes a first controller that centrally controls the elements forming the oral measurement apparatus 1D. The first controller includes a memory in which a program is stored and a processing circuit corresponding to a processor, such as a CPU. In the first controller, the processor executes the program stored in the memory. In the fourth embodiment, the first controller controls the sensor 11, the processor 21, the temperature information obtaining section 22, and the first communication unit 34.

{Processing Device}

The processing device 40 receives information from the oral measurement apparatus 1D and calculates the amount of moisture based on the received information. More specifically, the processing device 40 calculates the amount of moisture based on the information indicating the frequency converted from the electrostatic capacity in the processor 21. The processing device 40 also corrects the amount of moisture based on the calculated amount of moisture and temperature information concerning the processor 21. In an exemplary aspect, the processing device 40 is a computer. The processing device 40 may be a mobile terminal, such as a smartphone or a tablet terminal, or may be a server connected to a network.

The processing device 40 includes a second communication unit 41, a calculator 31, a correction processor 32, and an operation display unit 33. The calculator 31, the correction processor 32, and the operation display unit 33 are similar to those of the first embodiment, except for the operation of the operation display unit 33, and a detailed explanation thereof will be omitted. In the fourth embodiment, the provision of the operation display unit 33 in the processing device 40 may be omitted.

The second communication unit 41 communicates with the oral measurement apparatus 1D. More specifically, the second communication unit 41 receives the processing result and temperature information from the first communication unit 34 of the oral measurement apparatus 1D.

The second communication unit 41 includes a circuit for communicating with the oral measurement apparatus 1D in compliance with a predetermined communication standard. Examples of the predetermined communication standard are a LAN, Wi-Fi®, Bluetooth®, a USB, an HDMI, a CAN, and an SPI.

The processing device 40 receives the processing result and temperature information from the oral measurement apparatus 1D via the second communication unit 41. In the fourth embodiment, the processing device 40 receives digital information indicating the frequency and temperature information from the oral measurement apparatus 1D via the second communication unit 41.

In the processing device 40, the calculator 31 calculates the amount of moisture based on the frequency information and sends information indicating the calculated amount of moisture to the correction processor 32. The correction processor 32 corrects the amount of moisture based on the moisture amount information and temperature information concerning the processor 21. Information indicating the corrected amount of moisture is sent to the operation display unit 33 and is displayed.

The processing device 40 includes a second controller that centrally controls the elements forming the processing device 40. The second controller includes a memory in which a program is stored and a processing circuit corresponding to a processor, such as a CPU. In the second controller, the processor executes the program stored in the memory. In the fourth embodiment, the second controller controls the calculator 31, the correction processor 32, the operation display unit 33, and the second communication unit 41.

The oral measurement system 50 according to the fourth embodiment achieves the following advantages.

The oral measurement system 50 includes the oral measurement apparatus 1D extending in the longitudinal direction D1 and the processing device 40 which communicates with the oral measurement apparatus 1D. The oral measurement apparatus 1D includes the sensor 11, the processor 21, the temperature information obtaining section 22, and the first communication unit 34. The sensor 11 is disposed at the first end E1 (e.g., one end) of the oral measurement apparatus 1D in the longitudinal direction D1 and obtains analog information inside a mouth. The processor 21 is disposed close to the sensor 11 with respect to the central portion C1 of the oral measurement apparatus 1D in the longitudinal direction D1. The processor 21 converts the analog information obtained by the sensor 11 into digital information and outputs the digital information as a processing result. The temperature information obtaining section 22 obtains temperature information concerning the processor 21 and outputs the temperature information. The first communication unit 34 sends the processing result and temperature information to the processing device 40. The processing device 40 includes the second communication unit 41, the calculator 31, and the correction processor 32. The second communication unit 41 receives the processing result and the temperature information from the first communication unit 34 of the oral measurement apparatus 1D. The calculator 31 calculates the amount of moisture based on the processing result. The correction processor 32 corrects the calculated amount of moisture based on the moisture amount information and temperature information.

With this configuration, based on the information obtained by the oral measurement apparatus 1D, the amount of moisture can be calculated and also be corrected in the processing device 40. More specifically, the calculated amount of moisture can be corrected based on the temperature information concerning the processor 21.

Although the operation display unit 33 is provided in the processing device 40 in the fourth embodiment, it may be omitted. The operation display unit 33 may be disposed in the oral measurement apparatus 1D or in an external device different from the oral measurement system 50.

Although the oral measurement system 50 measures the amount of moisture in the fourth embodiment, it may measure the amount or the level of another subject in the mouth according to the exemplary aspects discussed above.

Each of the oral measurement apparatus and the oral measurement system according to exemplary embodiments of the present disclosure may be applicable to an oral measurement apparatus that measures the amount of moisture in a mouth.

While preferred embodiments of the invention have been described above with reference to the accompanying drawings, it is to be understood that variations and modifications will be apparent to those skilled in the art without departing from the scope and spirit of the invention.

What is claimed:

1. An oral measurement apparatus extending in a longitudinal direction, the oral measurement apparatus comprising:
   a sensor that is disposed at a first end of the oral measurement apparatus in the longitudinal direction and that is configured to obtain analog information inside a mouth;
   a processor that is disposed closer to the sensor with respect to a central portion of the oral measurement apparatus in the longitudinal direction and that is configured to convert the analog information obtained by the sensor into digital information as a processing result;
   a temperature information obtaining circuitry configured to obtain temperature information indicating a temperature of the processor and to output the temperature information; and a correction processor configured to correct the processing result based on at least the temperature information indicating the temperature of the processor.

2. The oral measurement apparatus according to claim 1, further comprising a casing constructed to house the sensor, the processor, and the temperature information obtaining circuitry therein.

3. The oral measurement apparatus according to claim 2, wherein the casing comprises:
   a sensor unit disposed close to the first end of the oral measurement apparatus in the longitudinal direction;
   a holding portion disposed close to a second end of the oral measurement apparatus in the longitudinal direction, with the second end being opposite the first end; and
   a probe unit having a bar-like shape that connects the sensor unit to the holding portion with the probe unit being interposed therebetween.

4. The oral measurement apparatus according to claim 3, wherein the
sensor unit includes the sensor, and the processor and the temperature information obtaining circuitry are disposed within the probe unit.

5. The oral measurement apparatus according to claim 4, wherein the temperature information obtaining circuitry is disposed closer to the second end of the oral measurement apparatus in the longitudinal direction than the processor.

6. The oral measurement apparatus according to claim 1, wherein the processor is coupled to the temperature information obtaining circuitry by a heat transfer member.

7. The oral measurement apparatus according to claim 6, wherein the heat transfer member comprises one of a substrate, a metal member, silicone, and carbon.

8. The oral measurement apparatus according to claim 7, wherein the heat transfer member comprises a ground pattern of the substrate.

9. The oral measurement apparatus according to claim 1, further comprising a heat transfer resin member that seals the processor and the temperature information obtaining circuitry.

10. The oral measurement apparatus according to claim 1, wherein the processor is further configured to calculate a level of a subject in the mouth based on the processing result output from the processor.

11. The oral measurement apparatus according to claim 10, wherein the a correction processor is further configured to correct the calculated level of the subject based on information indicating the calculated level of the subject and the temperature information.

12. The oral measurement apparatus according to claim 10, wherein the level of the subject is an amount of moisture.

13. The oral measurement apparatus according to claim 1, wherein the sensor comprises a capacitive sensor configured to obtain information indicating an electrostatic capacity as the analog information.

14. The oral measurement apparatus according to claim 13, wherein the processor comprises a frequency converter that is configured to convert the information indicating the electrostatic capacity into a frequency indicating a charge and discharge cycle of the sensor.

15. The oral measurement apparatus according to claim 6, wherein the heat transfer member comprises a substrate with the processor embedded therein.

16. An oral measurement system comprising:
an oral measurement apparatus extending in a longitudinal direction and including:
a sensor that is disposed at a first end of the oral measurement apparatus in the longitudinal direction and is configured to obtain analog information inside a mouth,
a processor that is disposed closer to the sensor with respect to a central portion of the oral measurement apparatus in the longitudinal direction and that is configured to convert the analog information obtained by the sensor into digital information as a processing result,
temperature information obtaining circuitry configured to obtain temperature information indicating a temperature of the processor, and
a first communication unit configured to transmit the processing result and the temperature information; and
a processing device configured to communicate with the oral measurement apparatus, the processing device including:
a second communication unit that receives the processing result and the temperature information from the first communication unit,
calculating circuitry configured to calculate a level of a subject in the mouth based on the processing result, and
a correction processor configured to correct the calculated level of the subject based on information indicating the calculated level of the subject and the temperature information indicating the temperature of the processor.

17. The oral measurement system according to claim 16, wherein the level of the subject is an amount of moisture.

18. The oral measurement system according to claim 16, wherein the temperature information obtaining circuitry is disposed closer to a second end of the oral measurement apparatus in the longitudinal direction than the processor, with the second end being opposite the first end.

19. The oral measurement system according to claim 16, wherein the processor is coupled to the temperature information obtaining circuitry by a heat transfer member.

20. The oral measurement system according to claim 19, wherein the heat transfer member comprises one of a substrate, a metal member, silicone, and carbon, and the heat transfer member forms a ground pattern of the substrate.

* * * * *